United States Patent
Su et al.

(10) Patent No.: US 10,420,501 B2
(45) Date of Patent: Sep. 24, 2019

(54) SLEEP MONITORING

(71) Applicant: KONINKLIJKE PHILIPS N.V., Eindhoven (NL)

(72) Inventors: Jing Su, Eindhoven (NL); Rainer Hilbig, Eindhoven (NL); Jun Shi, Eindhoven (NL); Huibin Wei, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 15/752,740

(22) PCT Filed: May 8, 2017

(86) PCT No.: PCT/EP2017/060886
§ 371 (c)(1),
(2) Date: Feb. 14, 2018

(87) PCT Pub. No.: WO2017/194450
PCT Pub. Date: Nov. 16, 2017

(65) Prior Publication Data
US 2019/0059807 A1   Feb. 28, 2019

(30) Foreign Application Priority Data

May 9, 2016 (WO) ............... PCT/CN2016/081426
Aug. 30, 2016 (EP) ..................................... 16186206

(51) Int. Cl.
*A61B 5/08* (2006.01)
*A61M 21/02* (2006.01)
(Continued)

(52) U.S. Cl.
CPC .......... *A61B 5/4812* (2013.01); *A61B 5/0002* (2013.01); *A61B 5/082* (2013.01);
(Continued)

(58) Field of Classification Search
CPC ..... A61B 5/4812; A61B 5/0002; A61B 5/082; A61B 5/0836; A61B 5/4809;
(Continued)

(56) References Cited

U.S. PATENT DOCUMENTS 7,108,659 B2 * 9/2006 Ross ..................... A61B 5/083
600/529
7,207,947 B2 * 4/2007 Koh ................... A61N 1/36557
600/529
(Continued)

FOREIGN PATENT DOCUMENTS

CN   203101953 U   7/2013
CN   204033325 U   12/2014
(Continued)

OTHER PUBLICATIONS

N. Goel, H. Kim, and R.P. Lao. An olfactory stimulus modifies nighttime sleep in young men and women. Chronobiology international, 22(5):889-904, 2005.
(Continued)

*Primary Examiner* — Navin Natnithithadha

(57) ABSTRACT

A sleep monitoring system (10) for monitoring the sleep of a subject is disclosed. The system comprises a $CO_2$ sensor (21) and a processor (31) communicatively coupled to the $CO_2$ sensor, wherein the processor is adapted to monitor a $CO_2$ concentration from sensor data produced by the $CO_2$ sensor; and derive sleep pattern information from the monitored $CO_2$ concentration, wherein the sleep pattern information comprises at least an indication that the subject is awake and an indication that the subject is asleep. A sleep monitoring method and computer program product are also disclosed.

17 Claims, 8 Drawing Sheets

(51) Int. Cl.
*A61B 5/00* (2006.01)
*A61B 5/083* (2006.01)
*A61M 21/00* (2006.01)

(52) U.S. Cl.
CPC .......... *A61B 5/0836* (2013.01); *A61B 5/4809* (2013.01); *A61M 21/02* (2013.01); *A61B 5/4836* (2013.01); *A61B 5/746* (2013.01); *A61B 2562/0204* (2013.01); *A61B 2562/0233* (2013.01); *A61M 2021/0016* (2013.01); *A61M 2021/0027* (2013.01); *A61M 2021/0044* (2013.01); *A61M 2021/0066* (2013.01); *A61M 2205/18* (2013.01); *A61M 2205/3569* (2013.01); *A61M 2205/3584* (2013.01); *A61M 2205/3592* (2013.01); *A61M 2205/502* (2013.01); *A61M 2205/52* (2013.01); *A61M 2230/432* (2013.01)

(58) Field of Classification Search
CPC .................. A61B 5/4836; A61B 5/746; A61B 2562/0204; A61B 2562/0233; A61M 21/02; A61M 2021/0016; A61M 2021/0027; A61M 2021/0044; A61M 2021/0066; A61M 2205/18; A61M 2205/3569; A61M 2205/3584; A61M 2205/3592; A61M 2205/502; A61M 2205/52; A61M 2230/432
USPC .......................................... 600/529, 532–538
See application file for complete search history.

(56) References Cited

U.S. PATENT DOCUMENTS

| | | | |
|---|---|---|---|
| 8,979,730 | B2 | 3/2015 | Naujokat |
| 10,206,573 | B2 * | 2/2019 | Jeong ................. G06K 9/00362 |
| 2011/0190594 | A1 | 8/2011 | Heit |
| 2013/0018284 | A1 | 1/2013 | Kahn |
| 2013/0046151 | A1 | 2/2013 | Bsoul et al. |
| 2013/0066226 | A1 | 3/2013 | Baloa |
| 2013/0096404 | A1 | 4/2013 | Colman |
| 2015/0289802 | A1 | 10/2015 | Thomas |
| 2016/0015315 | A1 | 1/2016 | Auphan |
| 2018/0235471 | A1 * | 8/2018 | Jeong ................. G06K 9/00362 |

FOREIGN PATENT DOCUMENTS

| | | |
|---|---|---|
| CN | 104434068 A | 3/2015 |
| FR | 2947712 A1 | 1/2011 |
| JP | 2015108469 A | 6/2015 |
| KR | 19990015607 U | 5/1999 |
| WO | 2012156427 A1 | 11/2012 |
| WO | 2016004399 A1 | 1/2016 |
| WO | 2015064547 A1 | 3/2017 |

OTHER PUBLICATIONS

L. Harmat, J. Takacs, and R. Bodizs. Music improves sleep quality in students. Journal of Advanced Nursing, 62 (3):327-335, 2008.
Robert L. Owens, Prespiratory Care, 2013. pp. 32-44.
Swedlow Db., Capnometry and Capnograpny: The Anesthesia Disaster Early Warning System, Seminars in Anesthesia, 1986; vol. 3, pp. 194-205.
Kazuyo Tsuzuki & Hiroko Kubo, Special Issues No. 3 : Measurement Technique for Ergonomics, Section 2 : Measurements of Human Response Effected by the Ambient Environment (1) Thermal Environment, Thermoregulation, and Thermal Comfort, Feb. 15, 2015. (English not available).
Suzuki, S. Nagamine, S. Kitagawa, Energy Metabolism During Sleep (Report I), pp. 170-173.
S. Suzuki, S. Nagamine, S. Kitagawa, S. Oshima, Energy Metabolism During Sleep (Report II), Sleeping Metabolism in Autumn, pp. 97-101.

* cited by examiner

SLEEP MONITORING

This application is the U.S. National Phase application under 35 U.S.C. § 371 of International Application No. PCT/EP2017/060886, filed on May 8, 2017, which claims the benefit of International Application No. 16186206.5 filed on Aug. 30, 2016 and International Application No. PCT/CN2016/081426 filed May 9, 2016. These applications are hereby incorporated by reference herein.

FIELD OF THE INVENTION

The present invention relates to a sleep monitoring system for monitoring the sleep of a subject.

The present invention further relates to a method of monitoring the sleep of a subject.

The present invention yet further relates to a computer program product that facilitates the monitoring of the sleep of a subject.

BACKGROUND OF THE INVENTION

Sleep is a critical part of our lives. It ensures that our bodies rest and can repair and is therefore crucial for long-term health. It is therefore important that people, i.e. subjects, sleep properly. Without proper sleep, chronic health issues may arise. For this reason, many solutions have been proposed that facilitate the monitoring of sleep by a subject, for example to diagnose sleep disorders or to improve the sleep process by creating an atmosphere in a confined space in which the subject is sleeping to improve the quality of sleep for that subject.

For example, CN 203101953 A discloses a device that comprises a brainwave detecting means to detect the brainwaves of a subject and a controller arranged to analyze these brainwaves to detect various sleep stages, with the device arranged to control an air conditioner, humidifier and/or lighting controller to improve the sleep of that subject in response to a detected sleep stage.

US2016/015315 A1 discloses a sleep assist system to monitor and assist the user's sleep. The system provides an alert to third person when the system is used by people with medical condition, elderly people and/or pregnant women, and an unexpected situation occurs. The sensing unit, the bedside device and a mobile terminal monitor the sleep cycles and/or improve the user's sleep. The system provides the user with improved understanding of individual sleep patterns and information about environment affects sleep quality.

US2011/190594 A1 discloses an arrangement for monitoring a patient's sleep activity. The arrangement provides a more accurate diagnosis and more effective treatment while reducing the required clinician time per patient for treatment delivery since a communication apparatus enables the healthcare professional to remotely communicate and assess the patient. Allows both duration and frequency of change of conditions to be measured since the display and processing unit keeps track of the point in time at which a change of the environmental condition or condition of the patient occurs.

A drawback of such devices is that they require physical contact with the subject attempting to sleep. Similar solutions, e.g. solutions in which pressure sensors or the like are fitted to a mattress on which a subject is attempting to sleep, to an extent suffer from the same problem or may suffer from accuracy problems. This physical contact can be perceived as uncomfortable and as such cause a disruption of the sleep of the subject being monitored. Hence, there exists a need for a sleep monitoring system that can monitor sleep in a more unobtrusive manner.

SUMMARY OF THE INVENTION

The present invention seeks to provide a sleep monitoring system that does not require physical contact with the subject sleeping to obtain accurate sleep information.

The present invention further seeks to provide a method of monitoring the sleep of a subject that does not require physical contact with the subject sleeping to obtain accurate sleep information.

The present invention yet further seeks to provide a computer program product that facilitates the implementation of such a method on a computing device.

According to an aspect, there is provided a sleep monitoring system for monitoring the sleep of a subject, comprising a $CO_2$ sensor and a processor communicatively coupled to the $CO_2$ sensor, wherein the processor is adapted to monitor a $CO_2$ concentration from sensor data produced by the $CO_2$ sensor; and derive sleep pattern information from the monitored $CO_2$ concentration, wherein the sleep pattern information comprises at least an indication that the subject is awake and an indication that the subject is asleep.

The present invention is based on the insight that the amount of $CO_2$ expelled by a subject, i.e. a person, which is a function of the state of activity of that subject, can be used to accurately determine whether the subject is awake or asleep. Consequently, by monitoring $CO_2$ levels with the sensor and processing the monitored $CO_2$ levels with the processor, sleep pattern information can be derived without having to contact the subject being monitored.

In an embodiment, the processor is adapted to provide an indication that the subject is awake when a rate of increase in the monitored $CO_2$ concentration is greater than a first threshold; and provide an indication that the subject is asleep when the rate of increase in the monitored $CO_2$ concentration is below the first threshold. For example, the processor may be adapted to determine the first threshold by in situ calibration of the sleep monitoring system.

The sleep monitoring system may further comprise a further sensor for producing an indication that the subject is attempting to sleep, wherein the processor is adapted to derive sleep pattern information from sensor data produced by the $CO_2$ sensor and the further sensor. This for instance is beneficial where the sleep monitoring system is configured to determine a sleep efficiency metric for the subject, where the sensor data provided by the further sensor may be used to determine the point in time at which the subject begins the attempt to fall asleep or to determine the point in time at which the subject wakes up. For example, the further sensor may be a light sensor, a sound sensor or a user interface sensor.

In an embodiment, the sleep pattern information further comprises an indication of the sleep efficiency. Such an indication may be used to determine the efficiency or quality of the sleep of the subject, which for example may be useful to determine if certain physical symptoms of the subject, e.g. chronic fatigue, may be explained by a disrupted sleep pattern.

The processor may be adapted to calculate the indication of the sleep efficiency from a first time period initiated by the indication that the subject is attempting to sleep and terminated by an indication that the subject is getting up; and a second time period initiated by an indication that the subject is asleep and terminated by an indication that the subject is awake that follows the indication that the subject is asleep.

In an embodiment, the processor is further adapted to identify a sleep phase from said sensor data for the subject from the monitored $CO_2$ concentration. By determining a particular sleep phase, e.g. light sleep or deep sleep, the sleep monitoring system is facilitated to optimize sleeping conditions of the subject.

To this end, the processor may be adapted to identify that the subject is awake when a rate of increase in the monitored $CO_2$ concentration is greater than the first threshold; identify a light sleep phase when a rate of increase in the monitored $CO_2$ concentration is between the first threshold and a second threshold;

and identify a deep sleep phase when a rate of increase in the monitored $CO_2$ concentration is below the second threshold.

The sleep monitoring system may be adapted to create a particular sleeping atmosphere in response to the determination of a particular sleep phase in order to optimize the sleeping conditions of the subject. For example, the sleep monitoring system may further comprise an output device for creating a sensory stimulus for said subject, wherein the processor is further adapted to generate a control signal for the output device in response to an identified sleep phase. For example, the output device may comprise at least one of a scent releasing device, an audio output device and a light output device.

The processor of the sleep monitoring device may be further adapted to generate a control signal for the output device by a defined amount of time prior to a wake-up time of the subject. In this manner, a pleasant atmosphere may be created for the subject to wake up in, which may improve the well-being of the subject when starting a new day.

The sleep monitoring system may comprise a plurality of different output devices for creating respective sensory stimuli, wherein processor is further adapted to generate a control signal for one or more selected output devices as a function of the identified sleep phase. In this manner, a dynamic sleeping environment and may be created in which various sensory stimuli are generated as a function of an identified sleep phase in order to create the optimal sleeping conditions for that particular sleep phase.

For example, the sleep monitoring system may further comprise a fan, wherein the processor is further adapted to generate a further control signal for said fan in response to an identified sleep phase.

In at least some embodiments, the sleep monitoring system is at least partially comprised by an air purification apparatus, a respirator apparatus or a humidification apparatus. This has the advantage that a dual purpose apparatus is provided, which apparatus may generate an atmosphere in a confined space in which the subject is sleeping that is tailored to a particular sleep stage of the subject by the inclusion of at least part of the sleep monitoring system in the apparatus.

In an embodiment, the sleep monitoring system comprises a first device comprising the $CO_2$ sensor and a second device comprising the processor, the first device and the second device each comprising a wireless communication module for establishing a wireless communication link between the first device and the second device, wherein the second device is a wearable device or a mobile communication device. Such a modular system is particularly flexible and for example allows for sleep monitoring data to be collected in a location separate to the sensor, such that a compact sensor may be provided that may be placed in close vicinity to the subject being monitored in order to improve the accuracy of the sleep monitoring.

According to another aspect, there is provided a method of monitoring the sleep of a subject, the method comprising receiving a measured $CO_2$ concentration; and deriving sleep pattern information from the measured $CO_2$ concentration, wherein the sleep pattern information comprises providing at least an indication that the subject is awake and an indication that the subject is asleep. With this method, valuable information about whether the subject is asleep not can be obtained without contacting the subject, which reduces the risk that the subject is disturbed by the sleep monitoring method.

Deriving the sleep pattern information may comprise providing an indication that the subject is awake when a rate of increase in the monitored $CO_2$ concentration is greater than a first threshold; and providing an indication that the subject is asleep when the rate of increase in the monitored $CO_2$ concentration is below the first threshold. This is a straightforward way of determining whether the subject is asleep or awake, with the first threshold being definable in a straightforward manner, e.g. through a calibration.

Deriving sleep pattern information may comprise determining a sleep efficiency or determining a sleep phase of said subject. For example, determining a sleep efficiency may comprise calculating an indication of the sleep efficiency from a first time period initiated by an indication that the subject is attempting to sleep and terminated by an indication that the subject is getting up; and a second time period initiated by an indication that the subject is asleep and terminated by an indication that the subject is awake that follows the indication that the subject is asleep. Such an indication of a sleep efficiency can provide valuable information about the sleep quality of the subject, which for example may be used to find a cause for certain physical symptoms such as chronic fatigue and/or to improve the sleeping conditions of the subject in order to improve the sleep efficiency.

In order to create a particularly suitable sleeping condition, the method may further comprise triggering the generation of a predefined sensory stimulus for said subject in response to the determined sleep phase of said subject. Such a predefined sensory stimulus may be a factory setting or alternatively, the method may comprise receiving a sensory stimulus program from a user; and generating the predefined sensory stimulus in accordance with the received sensory stimulus program such that the method may produce a sleeping atmosphere that is perceived as particularly pleasant by a particular user.

According to yet another aspect, there is provided a computer program product comprising a computer readable storage medium having computer readable program instructions embodied therewith for, when executed on a processor of a sleep monitoring system according to embodiments of the present invention, cause the processor to implement the method according to embodiments of the present invention. Such a computer program product facilitates the configuration of a pre-existing computing device as part of the sleep monitoring system according to embodiments of the present invention.

BRIEF DESCRIPTION OF THE DRAWINGS

Embodiments of the invention are described in more detail and by way of non-limiting examples with reference to the accompanying drawings, wherein FIG. 1 schematically depicts a sleep monitoring system according to an embodiment.

DETAILED DESCRIPTION OF THE EMBODIMENTS

Figure 1:
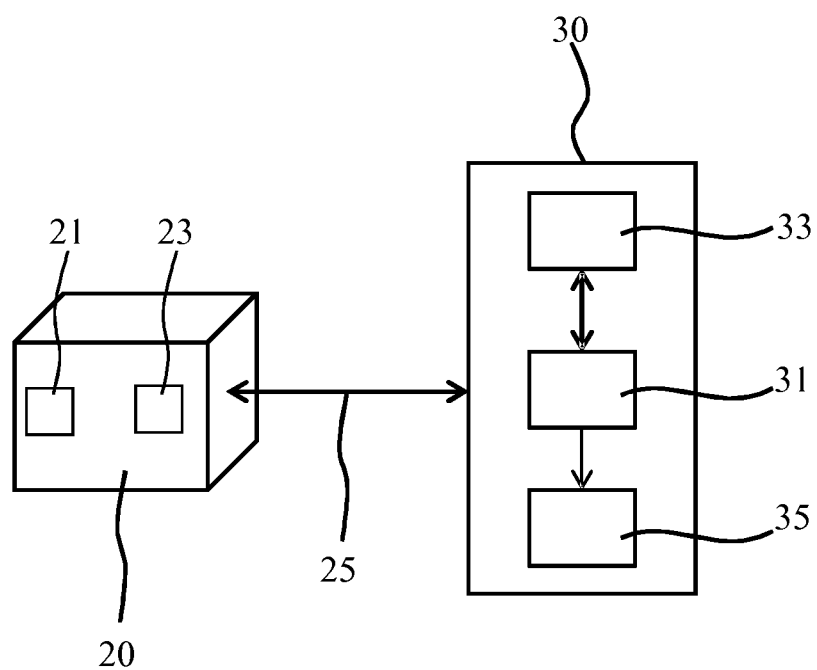

It should be understood that the Figures are merely schematic and are not drawn to scale. It should also be understood that the same reference numerals are used throughout the Figures to indicate the same or similar parts.

FIG. 1 schematically depicts a sleep monitoring system 10 according to an embodiment. The sleep monitoring system 10 is adapted to monitor the sleep of a subject in a confined space such as a bedroom in which a sensor device 20 of the sleep monitoring system 10 is positioned. The sensor device 20 at least comprises a $CO_2$ sensor 21 and may comprise one or more further sensors 23, which may include a light sensor, a sound sensor, e.g. a microphone, a user input sensor, e.g. a user interface, and so on.

The sensor device 20 may be a stand-alone device, e.g. a sensor box or the like that may be positioned in close vicinity to the subject to be monitored. For example, the sensor device 20 may be dimensioned such that it can be clipped or otherwise secured to a bed, e.g. to a headboard of the bed, in which the subject sleeps, such that a change in the $CO_2$ concentration caused by exhalation of $CO_2$ by the subject can be accurately monitored with the sensor device 20 before the $CO_2$ diffuses into the total volume of air within the confined space in which the sensor device 20 is positioned, e.g. a bedroom in which the subject sleeps. In alternative embodiments, the sensor device 20 may form part of an apparatus adapted to alter the condition of the atmosphere within the confined space as will be explained in more detail below. For example, such an apparatus may be adapted to adjust at least one of the purity, humidity, temperature and scent level in the atmosphere (air) in the confined space. Such functionality for example may be included in an air purification apparatus, an air conditioning apparatus, an air humidification apparatus, a scent release apparatus or any apparatus that includes one or more of the above functionality.

The sleep monitoring system 10 typically comprises a computing device 30 including a processor 31. As shown in FIG. 1, the computing device 30 may be a separate device to the sensor device 20. For example, the computing device 30 may be any suitable computing device, such as a personal computer, e.g. a desktop computer or a laptop computer, a tablet computer, a personal digital assistant, a mobile communication device such as a smartphone, a wearable smart device such as a smart watch, and so on. The computing device 30 may form an assembly with the sensor device 20. In such an assembly, the computing device 30 may be a discrete entity or may form part of an apparatus adapted to alter the condition of the atmosphere within the confined space, i.e. such an apparatus may comprise the processor 31. The processor 31 may be any suitable processor, e.g. a generic processor or an application-specific processor. The computing device 30 may further comprise a data storage device 33 communicatively coupled to the processor 31.

The computing device 30 is arranged to communicate with the sensor device 20 to obtain $CO_2$ levels in the confined space in which the subject is located as determined with the $CO_2$ sensor 21. The $CO_2$ sensor 21 and the further sensor(s) 23 if present are communicatively coupled to the computing device 30 over a communication link 25 such that the processor 31 can receive sensor readings from such sensors. Such a communication link may be a wired communication link, e.g. in case the sensors 21, 23 are integral to the computing device 30, or may be a wireless communication link, e.g. in case the sensors 21, 23 are located in a different device to the computing device 30, e.g. in a separate sensor device 20. To this end, the respective devices communicatively coupled over such a wireless communication link may include a wireless transceiver (not shown). The devices may communicate with each other through their respective wireless transceivers using any suitable wireless communication protocol, e.g. Bluetooth, Wi-Fi, a mobile communication protocol such as 2G, 3G, 4G or 5G, a suitable near-field communication (NFC) protocol or a proprietary protocol. In case of such wireless communication, the respective devices may communicate directly with each other or may communicate with each other through an intermediary such as a wireless bridge, a router, a hub, and so on. Any suitable embodiment of wired or wireless communication between such respective devices may be contemplated.

The processor 31 may be further communicatively coupled to a data storage device 33, here shown to form part of the computing device 30. Such a data storage device may be any suitable device for storing digital data, e.g. a random access memory, a cache memory, a Flash memory, a solid state storage device, a magnetic storage device such as hard disk, an optical storage device and so on. Alternatively, the data storage device 33 may be separate from the computing device 30, e.g. a network storage device or a cloud storage device accessible to the processor 31 over a network such as a LAN or the Internet. The processor 31 may store sensor data received from the connected sensors 21, 23 in the data storage device in order to collect and store historical sleep information obtained for the subject in the confined space, for example to analyze the sleep efficiency of that subject as will be explained in more detail below.

In FIG. 1, the computing device 30 further comprises a sensory output device 35 under control of the processor 31. Such a sensory output device may be any device that capable of producing an output that can be detected by one of the human senses. For example, the sensory output device 35 may be adapted to produce a visible or audible output. The processor 31 may be adapted to generate a control signal indicative of a determined sleep efficiency of the subject with the processor 31, which control signal triggers the sensory output device 35 to produce a sensory output indicating the determined sleep efficiency. For example, the sensory output device 35 may comprise a display adapted to display the determined sleep efficiency (or sleep efficiency history) of the subject.

Figure 2:
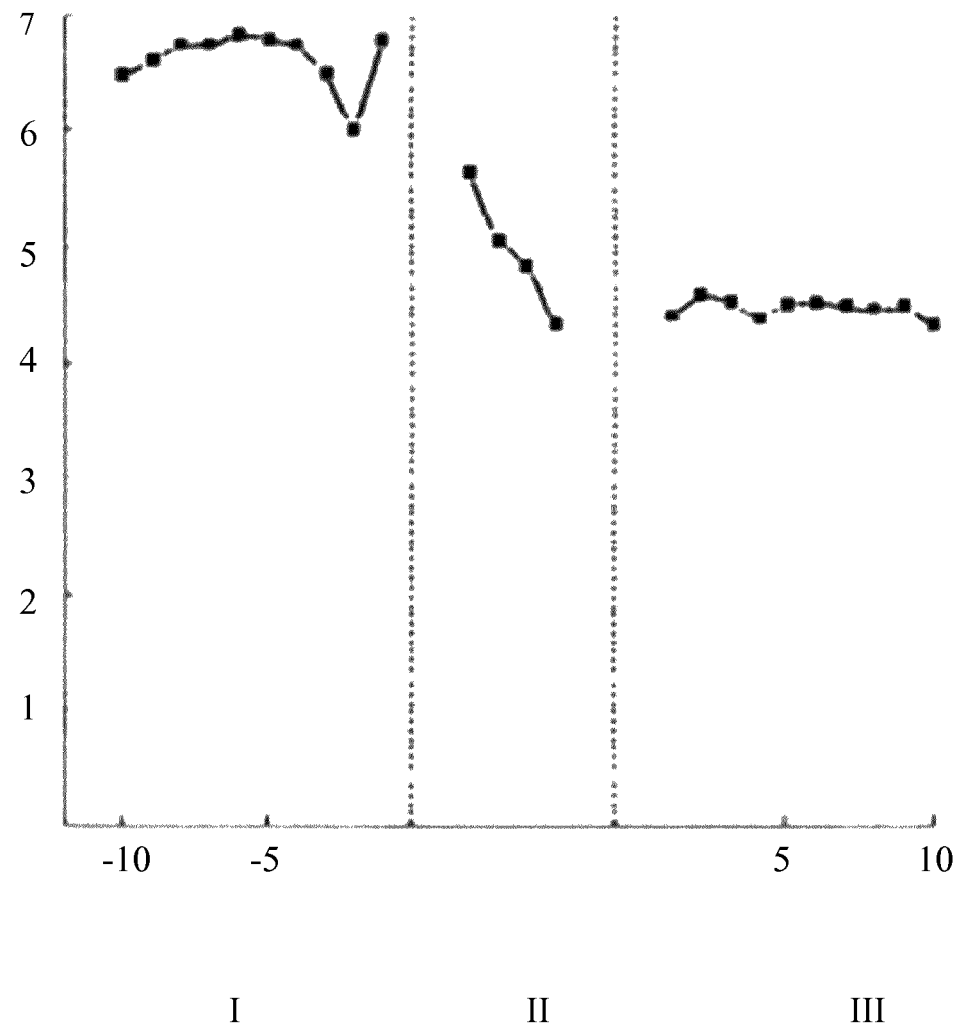
FIG. 2 is a graph depicting typical human ventilation volumes associated with different states of awareness.

FIG. 2 provides proof of concept of the ability to detect different states of awareness, i.e. a distinction between a subject being awake or asleep. FIG. 2 depicts a graph in which three sleep phases are identified. Phase I is awake, phase II is a transition to a state of sleep and phase III is a state of sleep, with the X-axis displaying time (in minutes) and the Y-axis displaying ventilation of the subject (in 1/min). This graph therefore clearly depicts a distinct decrease in ventilation (breathing) volumes upon the subject going from a state of being awake to a state of being asleep. Consequently, the amount of $CO_2$ expelled going from a state of being awake to a state of being asleep is therefore also reduced. The monitored amount of $CO_2$ expelled by a subject under monitoring during a unit period of time can be used as an indicator of whether the subject is awake or asleep. For example, if the amount of $CO_2$ expelled during such a unit period of time exceeds a defined threshold, this may be considered indicative of the subject being awake, whereas if the amount of $CO_2$ expelled during such a unit period of time falls below this defined threshold, this may be considered indicative of the subject being asleep.

Figure 3:
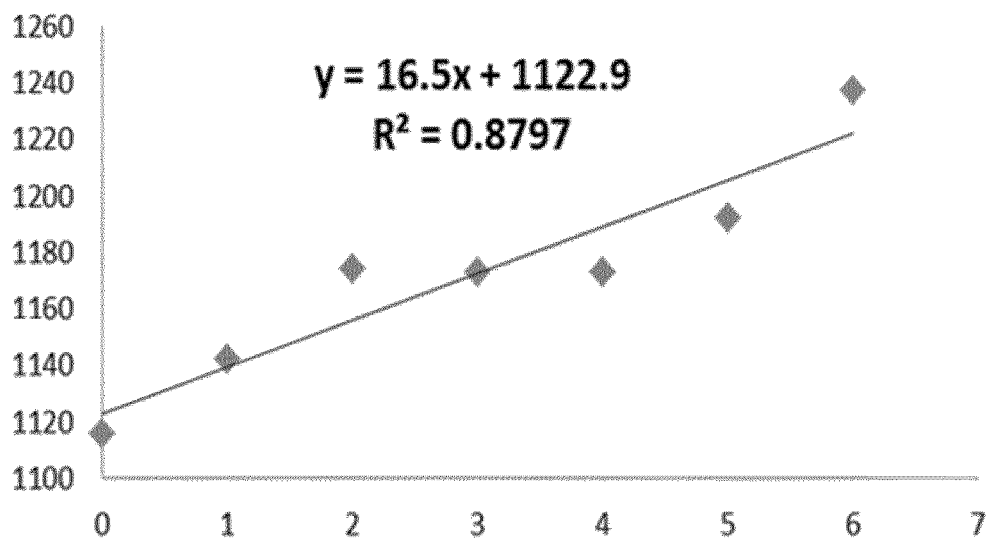
FIG. 3 is a graph depicting measured indoor $CO_2$ levels for a room in which a person is active.
Figure 4:
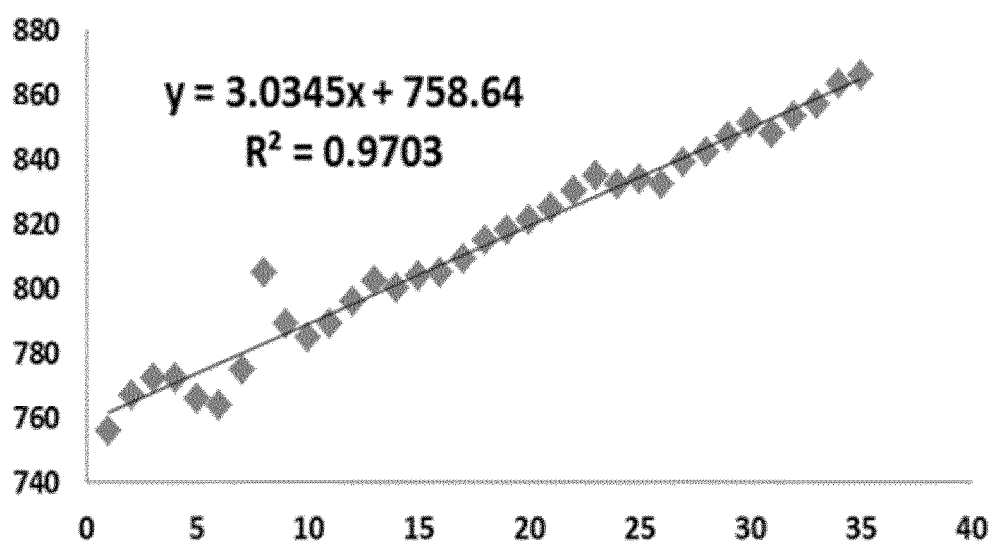
FIG. 4 is a graph depicting measured indoor $CO_2$ levels for a room in which a person is awake but resting.
Figure 5:
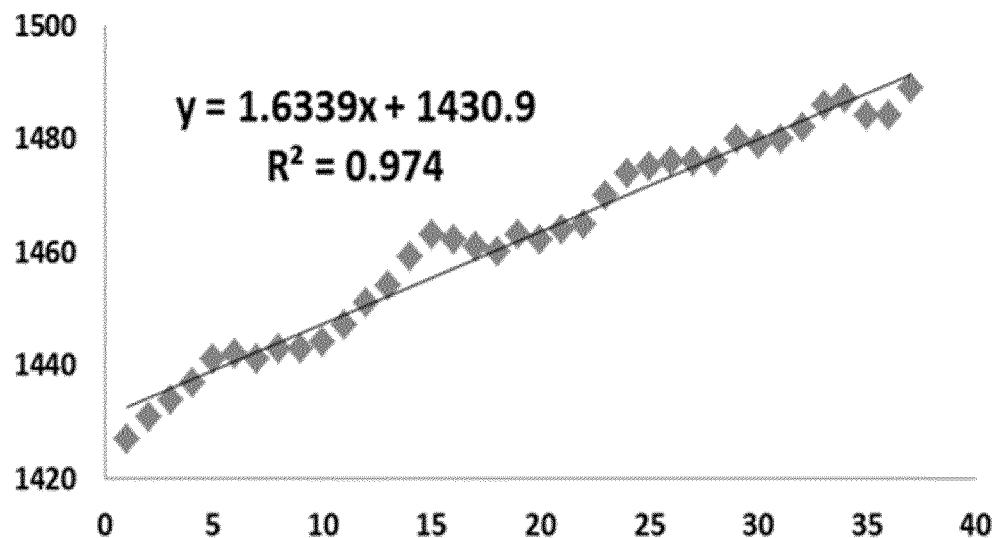
FIG. 5 is a graph depicting measured indoor $CO_2$ levels for a room in which a person is asleep.

The feasibility of using the monitoring of $CO_2$ levels to monitor the sleep of a subject is further demonstrated by FIG. 3-5, in which the levels of $CO_2$ expelled by a subject during exercise (FIG. 3), rest (FIG. 4) and sleep (FIG. 5) were monitored with a $CO_2$ sensor over a period of time within the same confined space (i.e. a space having a constant volume of 29.25 m$^3$), with hermetically sealed windows and doors to minimize the loss of $CO_2$ from the confined space. During exercise, the monitored $CO_2$ levels translated into a rate of $CO_2$ increase of 16.5 ppm/min. In a rest state (i.e. the subject being awake but resting), the monitored $CO_2$ levels translated into a rate of $CO_2$ increase of 3.0 ppm/min, whereas in a sleep state of the subject, the monitored $CO_2$ levels translated into a rate of $CO_2$ increase of 1.6 ppm/min.

As will be immediately understood, the absolute values of these rates of $CO_2$ increase are dependent of several factors such as volume of the confined space, bodyweight and/or lung capacity of the monitored subject, rate of loss of $CO_2$ from the confined space, and so on. However, the data in FIG. 3-5 clearly demonstrates that for a particular subject, a clear difference exists in the rate at which $CO_2$ levels rise in the confined space between the various physical states of the monitored subject. Consequently, it is clearly demonstrated that by determining the rate of increase of the $CO_2$ level and comparing this rate against a defined threshold, a determination can be made about the physical state of the monitored subject, e.g. whether the subject is awake or asleep.

Moreover, it is well-known per se that a person in a light state of sleep produces a higher volume of ventilation (breathing) per unit time compared to a person in a deep state of sleep, such that a distinction between a light sleep and a deep sleep of a monitored subject may also be made by monitoring a rate of increase of $CO_2$ levels in the confined space and comparing the determined rate of increase of $CO_2$ levels in the confined space against a further defined threshold, with a light sleep being detected when the determined rate of increase of $CO_2$ levels in the confined space is above the further defined threshold and a deep sleep being detected when the determined rate of increase of $CO_2$ levels in the confined space is below the further defined threshold.

In an embodiment, the sleep monitoring system 10 may be configured to determine a particular physical state of the monitored subject in accordance with Table 1 (threshold 1 being higher than threshold 2):

TABLE 1

| State | Threshold 1 | Threshold 2 |
|---|---|---|
| Awake | Above | Above |
| Light sleep | Below | Above |
| Deep Sleep | Below | Below |

As previously mentioned, the absolute values of threshold 1 and threshold 2 will depend from a number of factors, such as such as volume of the confined space, bodyweight and/or lung capacity of the monitored subject, rate of loss of $CO_2$ from the confined space, and so on. In an embodiment, the respective thresholds to be applied by the sleep monitoring system 10 may be obtained through calibration of the system. This may be achieved in any suitable manner. For example, at least the sensor device 20 of the sleep monitoring system 10 may be placed within the confined space and used to monitor the subject over a period of time, e.g. during a night, in which the subject sleeps within the confined space. The data collected with the sensor device 20 may be evaluated to identify typical changes in the rate of increase of $CO_2$ levels within the confined space, which typical changes will be indicative of a change in physical state of the subject, e.g. a transition from a state of being awake to a state of light sleep or a transition from a state of light sleep to a state of deep sleep. Consequently, the various physical states can be readily identified in the collected data, such that the applicable values of Threshold 1 and Threshold 2 associated with (transitions between) these various physical states can be readily derived from the collected data. In order to improve the accuracy of the thus extracted thresholds, the data collection during calibration may be repeated a number of times, e.g. over a number of nights. The sleep monitoring system 10 may have a calibration mode that can be user-activated. For example, the sleep monitoring system 10 may comprise a user interface, e.g. on the sensor device 20 or the computing device 30 that allows the user to activate the calibration mode, e.g. after installation of the sensor device 20 in the vicinity of the location in which the subject to be monitored intends to sleep.

In an embodiment, the sleep monitoring system 20 is adapted to determine the sleep efficiency of the subject being monitored. The sleep efficiency SE may be defined as follows:

$$SE = \frac{\Delta T_{sleep}}{\Delta T_{total}}$$

$\Delta T_{total}$ is the total time the subject is attempting to sleep, whereas $\Delta T_{sleep}$ is the total time the subject actually is asleep. $\Delta T_{total}$ may be defined as a first time period initiated by an indication that the subject is attempting to sleep and terminated by an indication that the subject is getting up. The indication that the subject is getting up typically follows an indication that the subject has been asleep although this is not strictly necessary; for example in a scenario where the subject did not manage to sleep at all, such an indication of the subject being asleep would not be obtained.

The total time $\Delta T_{total}$ may be determined in a number of ways. For example, the start point of this period may be determined by collecting an indication with a further sensor 23 that the subject is attempting to sleep. This for example may be a pressure sensor for detecting the subject entering the bed, which pressure sensor for instance may be attached to a pillow or mattress or the like. However, such an indicator may be less accurate if the subject initially engages in relaxing activities before attempting to sleep, such as reading or watching TV. Alternatively, the further sensor 23 may be a light sensor that detects a change in light level in the confined space. In this manner, if the subject switches off a light within the confined space such as a bedside lamp or the TV, this may be interpreted as an indication of the subject attempting to go to sleep, and such an indication may be an accurate indication from which the determination of the time period $\Delta T_{total}$ may be initiated. Similarly, a sound sensor such as a microphone may be used for this purpose, as the user switching off the TV or stopping reading may be detected by a reduction in noise levels within the confined space. In yet another embodiment, the subject may provide a user input on a user input sensor 23 of the sensor device 20, e.g. on the user interface, to provide a particularly accurate indication of the subject initiating attempting to sleep. The endpoint of the time period $\Delta T_{total}$ may be determined in a similar manner, for example by detecting an alarm going off, by the subject switching on a light, from an increase in the rate at which $CO_2$ is expelled by the subject is determined with the $CO_2$ sensor 21, and so on.

$\Delta T_{sleep}$ may be defined as a second time period initiated by an indication that the subject is asleep and terminated by an indication that the subject is awake that follows the indication that the subject is asleep. In case of a disrupted sleep pattern, the subject may experience a number of periods during which the subject is asleep. In such a scenario, the total period $\Delta T_{sleep}$ that the subject was asleep may be obtained by summing all periods during which it was determined that the subject was asleep.

As will be understood from the foregoing, the total time $\Delta T_{sleep}$ may be determined using the $CO_2$ sensor data collected with the sensor device 20. For example, the sensor device 20 may periodically sample the $CO_2$ levels in the confined space in which the subject is attempting to sleep, which periodic data may be used to determine the total time $\Delta T_{sleep}$. For example, the total time $\Delta T_{sleep}$ may be determined by counting the number of data points in the periodic data for which the rate of increase of the $CO_2$ level relative to the previously captured data point was below Threshold 1. Other suitable ways of determining $\Delta T_{sleep}$ from the collected sensor data will be immediately apparent to the skilled person. The sleep monitoring system 10 may be further refined, for example to factor in scenarios in which the monitored subject temporarily leaves the bed, e.g. for a toilet break or the like. To this end, the sleep monitoring system 10 for example may be configured to continue determining the time period $\Delta T_{total}$ if it is determined that the subject returns to bed within a defined period of time. This may be determined in any suitable manner, e.g. using sensor data provided by the $CO_2$ sensor 21 and/or one or more of the further sensors 23 as previously explained. Other refinement approaches will be apparent to the skilled person.

In an embodiment, the sleep monitoring system 10 is further adapted to calculate the sleep onset latency (SOL) for the monitored subject. The sleep onset latency may be defined as the time period between the point in time at which the subject attempts to go to sleep and the point in time at which the subject actually falls asleep. The point in time at which the subject attempts to go to sleep and the may be determined the point in time at which the subject actually falls asleep may be determined as previously explained.

In an embodiment, the sleep monitoring system 10 may be adapted to provide an indication of the calculated sleep efficiency SE, optionally including an indication of the sleep onset latency SOL, on the sensory output device 35 such that the monitored subject may be made aware of his or her sleep efficiency. To this end, the sensory output device 35 may be included in a computing device 30 that is portable, e.g. a tablet device or mobile communications device such as a smart phone, or wearable device, e.g. a smart watch or the like that may be worn by the monitored subject during sleep. This has the further advantage that if the sensor device 20 is separate to the computing device 30, a short range wireless communication between the sensor device 20 and the computing device 30 may be deployed, e.g. NFC or Bluetooth, which may be beneficial in terms of energy efficiency.

The sleep monitoring system 10 may be adapted to build a history of sleep efficiencies to allow evaluation of the sleep history of the subject to be monitored. For example, the processor 31 may be adapted to store sleep monitoring data and/or a sleep efficiency calculated from the sleep monitoring data in the data storage device 33. The sleep monitoring system 10 may comprise a display as the sensory output device 35 on which the sleep history stored in the data storage device 33 may be displayed. In this manner, a history of the sleep efficiency of the monitored subject may be displayed and evaluated, which may provide valuable insights into typical sleep behaviours of the monitored subject. Such insights for instance may be used to determine if certain physical symptoms of the monitored subject may be explained by the sleep efficiency of the monitored subject over a period of time.

Figure 6:
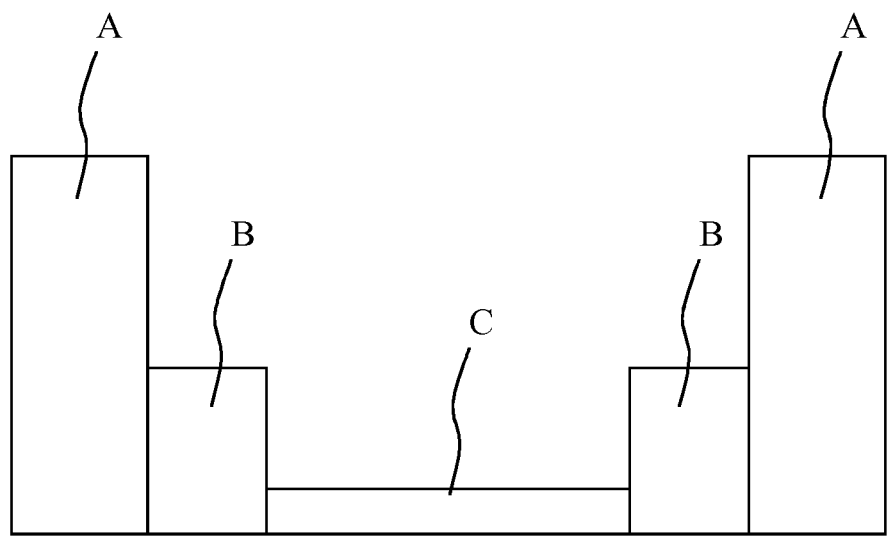
FIG. 6 is a block diagram schematically depicting the various sleep phases during a typical sleep cycle of a person.

In another embodiment, the sleep monitoring system 10 is adapted to create an optimized sleep ambience in which depending on the physical state of the monitored subject, e.g. the subject being awake, in a state of light sleep or in a state of deep sleep, the sleep monitoring system 10 is adapted to generate a sensory stimulus to support the sleeping process of the monitored subject. This is schematically depicted in FIG. 6, in which a state of being awake is labelled A, a state of light sleep is labelled B and a state of deep sleep is labelled C. The height of the various bars in FIG. 6 corresponds to a relative rate of $CO_2$ increase for a subject in the corresponding state and the width of each bar is an indication of the duration of that particular state.

Figure 7:
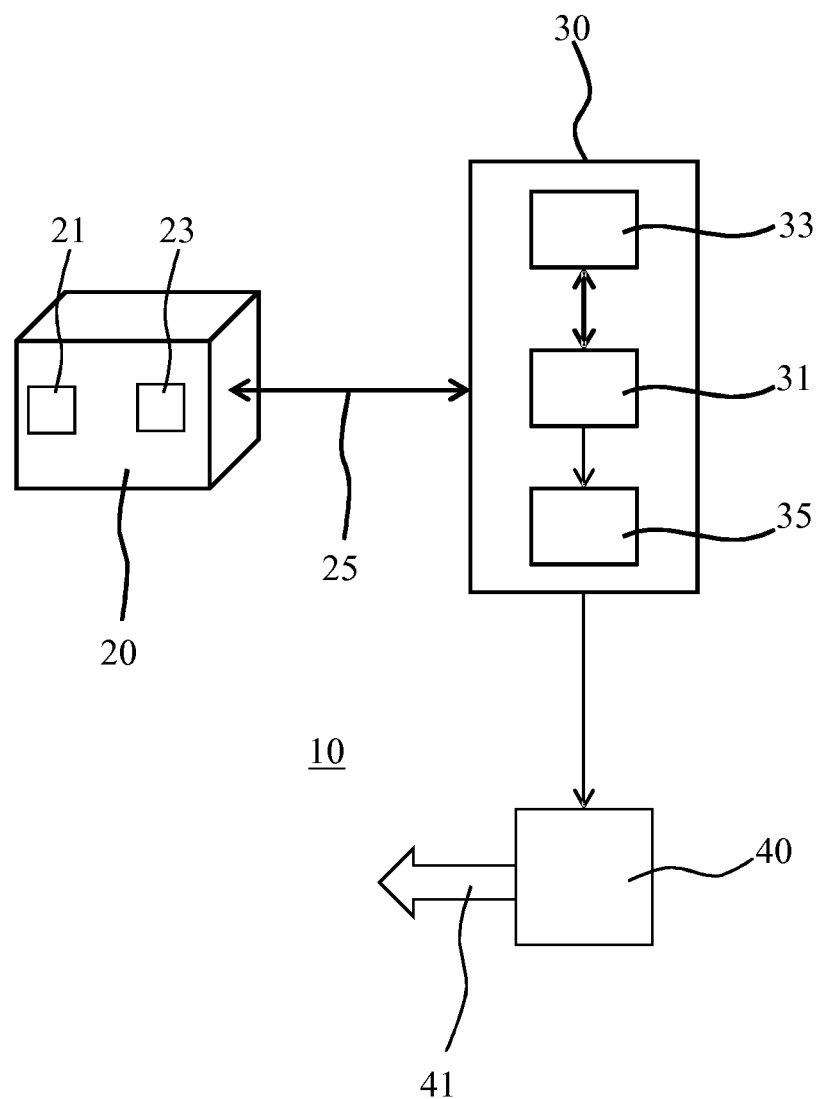
FIG. 7 schematically depicts a sleep monitoring system according to another embodiment.

FIG. 7 schematically depicts an embodiment of the sleep monitoring system 10 in which the sleep monitoring system 10 further comprises at least one sensory output device 40 adapted to generate a sensory stimulus 41 in response to a control signal provided by the computing device 30, e.g. by the processor 31. The processor 31 may be adapted to generate this control signal in response to an identified physical state, e.g. an identified sleep phase. In this context, it should be understood that a state of being awake is treated as a particular sleep phase, i.e. a phase of non-sleep. In response to sensor data provided by the sensor device 20, e.g. $CO_2$ levels indicative of the monitored subject entering a particular sleep phase, the processor 31 may generate the control signal to trigger the release of the sensory stimulus 41 by the sensory output device 40 in order to enhance or improve that particular sleep phase of the monitored subject.

The sensory output device 40 may be adapted to generate different types of sensory stimuli or alternatively the sleep monitoring system 10 may comprise a plurality of sensory output devices 40 each responsive to a control signal generated by the computing device 30 such that for different sleep phases, the processor 31 may trigger the generation of different types of sensory stimuli.

An example of a sensory stimulus that may enhance or improve a particular sleep mode is an audible stimulus such as the sound of wind, waves, a wind chime or any other type of sound that is considered calming by the monitored subject. In an embodiment, the sensory output device 40 may comprise a library of such sounds, with the sleep monitoring system 10 further comprising a user interface that facilitates the user selection of a particular sound from such a library.

Another example of a sensory stimulus that may enhance or improve a particular sleep mode is an olfactory stimulus such as a particular scent or smell that is perceived as pleasant and/or calming by the monitored subject, such as a perfume scent including lavender or pine tones, a breakfast smell that may be generated in the process of waking up the monitored subject, and so on. A sensory output device 40 adapted to provide such an olfactory stimulus, i.e. a scent releasing device, may be adapted to periodically emit the olfactory stimulus in order to retain a target level of the olfactory stimulus in the confined space. The sensory output device 40 adapted to provide such an olfactory stimulus may further be adapted to emit the olfactory stimulus at a user-specified rate.

To this end, the sleep monitoring system 10 may comprise a user interface that facilitates a user to specify the rate at which the olfactory stimulus is to be released by the sensory output device 40. In an embodiment, the sensory output device 40 adapted to provide such an olfactory stimulus may comprise a library of olfactory stimuli, i.e. several reservoirs containing chemical compounds for generating such an olfactory stimulus, with the sleep monitoring system 10 comprising a user interface that facilitates the monitored subject to select a particular olfactory stimulus to be generated during a particular sleep phase of that subject. Any suitable scent releasing device may be deployed as a sensory output device 40.

For example, the scent releasing device may comprise one or more cartridges loaded with a particular scent, which cartridges may be replaceable. The scent releasing device may comprise a nebulizer or the like to release the scent from the scent releasing device. Other well-known scent releasing mechanisms are equally applicable.

Yet another example of a sensory stimulus that may enhance or improve a particular sleep mode is an optical stimulus, e.g. light. For example, the sensory output device 40 may be a light output device under control of the computing device 30.

Yet another example of a sensory stimulus that can enhance or improve a particular sleep mode is an air condition. Such an air condition may be generated by an air conditioning apparatus that may adjust at least one of the temperature and humidity of an atmosphere within the confined space in which the monitored subject is sleeping. In an embodiment, the computing device 30 may be adapted to adjust a fan in such an apparatus, e.g. to reduce fan speed once the monitored subject has fallen asleep as the reduced volume of exhalation means that the requirement of conditioning the air within the confined space may be relaxed at this stage, or because reduce noise levels are desirable during sleep to reduce the risk of the monitored subject waking up by the noise of the fan.

In this manner, a sleep atmosphere may be created that is conducive to a healthy sleep pattern of the monitored subject. For example, during the initial stages of the subject's sleep, e.g. during the period of time in which the subject is trying to fall asleep, a calming atmosphere may be created using a particular scent and/or one or more calming sounds, which may be continued up to the point where it is determined from the measurements provided by the $CO_2$ sensor 20 as previously explained that the monitored subject has entered a state of light sleep or deep sleep. At this point, the sleep atmosphere may be modified by terminating the generation of the particular scent and/or one or more calming sounds and by adjusting, e.g. reducing, the airflow produced with an air conditioning unit of the sleep monitoring system 10. Such a sleep atmosphere may be predefined within the sleep monitoring system 10.

The sleep monitoring system 10 may comprise a library of such a sleep atmospheres as well as a user interface that allows the user selection of a particular sleep atmosphere from this library. In such an embodiment, the processor 31 is typically adapted to generate the control signals for the one or more sensory output devices 40 in accordance with the user-selected sleep atmosphere and the sensor signals provided by the sensor device 20, i.e. indicators of the subject attempting to go to sleep and entering particular sleep phases as explained in more detail above.

Alternatively, the sleep monitoring system 10 may be programmable to allow a user to program a personalized sleep atmosphere into the sleep monitoring system 10, in which case the processor 31 is typically adapted to generate a control signals for the one or more sensory output devices 40 in accordance with the specified personalized sleep atmosphere and the sensor signals provided by the sensor device 20, i.e. indicators of the subject attempting to go to sleep and entering particular sleep phases as explained in more detail above.

In an embodiment, the sleep monitoring system 10 may be further adapted to create a particular atmosphere prior to a wake-up time of the monitored subject to ensure that the monitored subject is pleasantly woken up. For example, the monitored subject by specify a wake-up time on a user interface of the sleep monitoring system 10, with the processor 31 adapted to generate a further control signal for one or more of the sensory output devices 40 a predefined amount of time prior to this wake-up time to cause the generation of this particular atmosphere in the confined space. Such a particular atmosphere for example may comprise a gradual increase in airflow generated with an air conditioning unit of the sleep monitoring system 10, a change in temperature within the confined space, generation of the smell of fresh coffee or another pleasant smell associated with waking up, and so on. Any combination of such sensory stimuli may be contemplated. The generation of the particular atmosphere may be used instead of an audible alarm or may be used in combination with an audible alarm, e.g. an alarm generated by an alarm clock or the like.

In an embodiment, the sleep monitoring system 10 may include intelligent software that evaluates the historical sleep data collected by the processor 31 to derive a typical wake-up pattern for the monitored subject, e.g. a particular wake-up time during weekdays and a particular wake-up time during weekends. In this embodiment, once the sleep monitoring system 10 has learned the typical wake-up behavior of the monitored subject, the monitored subject no longer needs to specify a particular wake-up time as the sleep monitoring system 10 can autonomously determine the appropriate point in time at which the pleasant wake-up atmosphere may be generated.

In FIG. 7, the one or more sensory output devices 40 are discrete devices that are separate to the computing device 30 and/or the sensor device 20. In this embodiment, the one or more sensory output devices 40 may be communicatively coupled to the computing device 30 in any suitable manner, e.g. through wireless or wired communication as explained above for the communication channel 25. However, it is equally feasible that at least some of the one or more sensory output devices 40 form part of the apparatus that further includes the computing device 30 and/or the sensor device 20. For example, such an apparatus may be an an air conditioning apparatus, an air purification apparatus, a respirator apparatus or a humidification apparatus.

Figure 8:
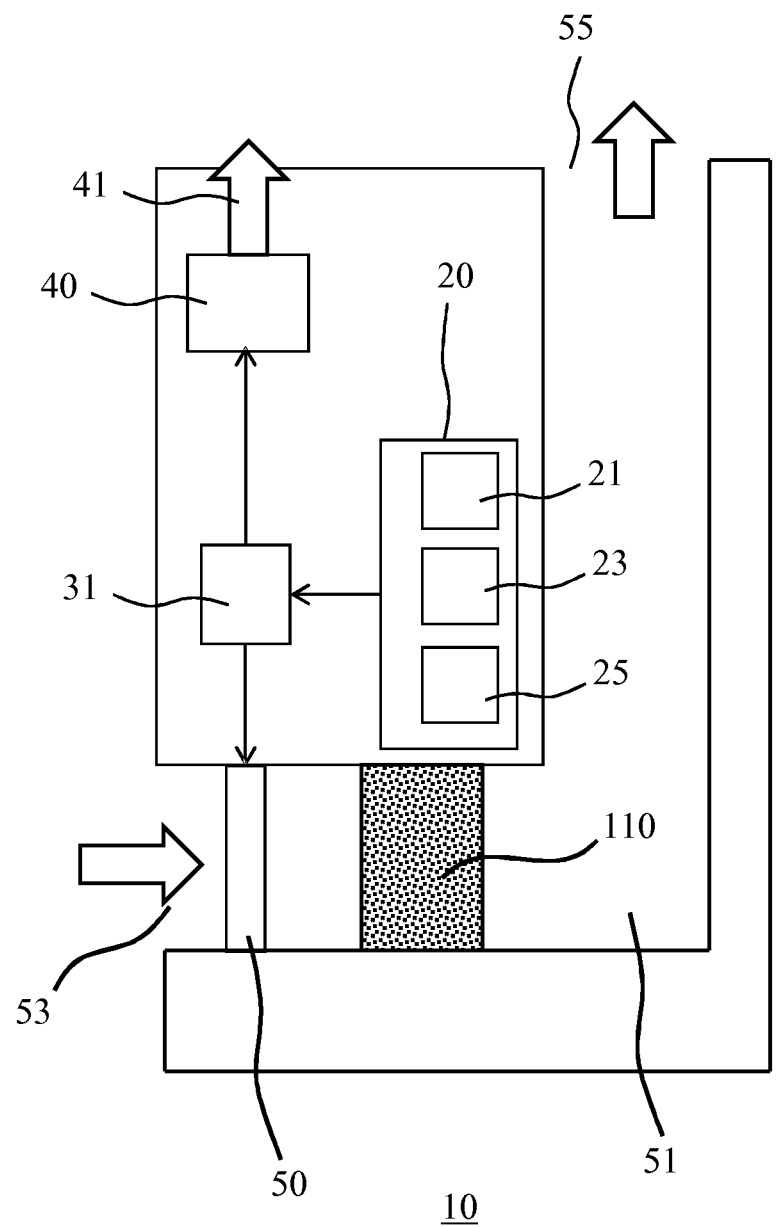
FIG. 8 schematically depicts a sleep monitoring system according to yet another embodiment.

FIG. 8 schematically depicts an example embodiment of a sleep monitoring system 10 embodied by an air purification apparatus having an air inlet 53, an air outlet 55 and an air purification path 51, e.g. a fluid conduit, extending between the air inlet 53 and the air outlet 55. A fan 50 may be located in the air purification path 51 to control the flow rate of air through the air purification path 51. The fan 50 may be controlled by the processor 31 integral to the air purification apparatus. As previously explained, the processor 31 may be adapted to control a speed of the fan 50 in response to the detection of a particular sleep phase of the subject to be monitored. The sensor device 20 is also integral to the air purification apparatus in this embodiment and in addition to the previously described $CO_2$ sensor 21 and the one or more further sensors 23 may further comprise one or more additional sensors 25 for monitoring a pollution level in the air entering the air purification apparatus through the air inlet 53. The processor 31 may be further adapted to regulate the fan speed of the fan 50 in response to sensor data provided by the one or more additional sensors 25 to ensure that the air quality in the confined space in which the air purification apparatus is placed is appropriately regulated. As such sensor-based fan speed regulation is well-known per se, this is not further explained for the sake of brevity only.

The air purification apparatus further comprises one or more pollutant removal structures 110, e.g. filters or the like, as is well-known per se. This will therefore not be further explained for the sake of brevity only. The air purification apparatus further comprises one or more sensory output devices 40 for producing a sensory output 41 in response to a control signal provided by the processor 31 following the detection of a particular sleep phase by the processor 31 from the sensor data provided by the sensor device 20 as previously explained. It will be immediately understood by the skilled person that although such an integral sleep monitoring system 10 is explained in more detail for an air purification apparatus, it is equally feasible to implement such an integral sleep monitoring system 10 in similar air treatment apparatuses such as air conditioners, air humidifiers, respirator devices, and so on.

At this point, it is noted that embodiments of the sleep monitoring system 10 may also be used in a confined space in which multiple subjects are sleeping. For example, in such a scenario multiple sleep monitoring systems with ($CO_2$) sensing capability and sensory stimulus generation local to a particular subject may be deployed to create localized sleep atmospheres tailored to that particular subject. Alternatively, a single sleep monitoring system 10 comprising multiple sensors which may be deployed local to a particular subject to be monitored and comprising multiple outlets for a particular sensory stimulus may be contemplated. For example, the sleep monitoring system 10 may be configured to directionally release a sensory stimulus towards a particular subject, i.e. the monitored subject, such that in case of multiple subject in the same confined space only the monitored subject is primarily targeted by the sensory stimulus, thereby reducing the risk that other subjects experience the sensory stimulus (to a large degree).

Although embodiments of the present invention are described in the context of $CO_2$ monitoring, it should be understood that alternative embodiments in which another gas affected by ventilation (breathing), e.g. $O_2$, may be monitored, e.g. to support or replace $CO_2$ monitoring data.

Figure 9:
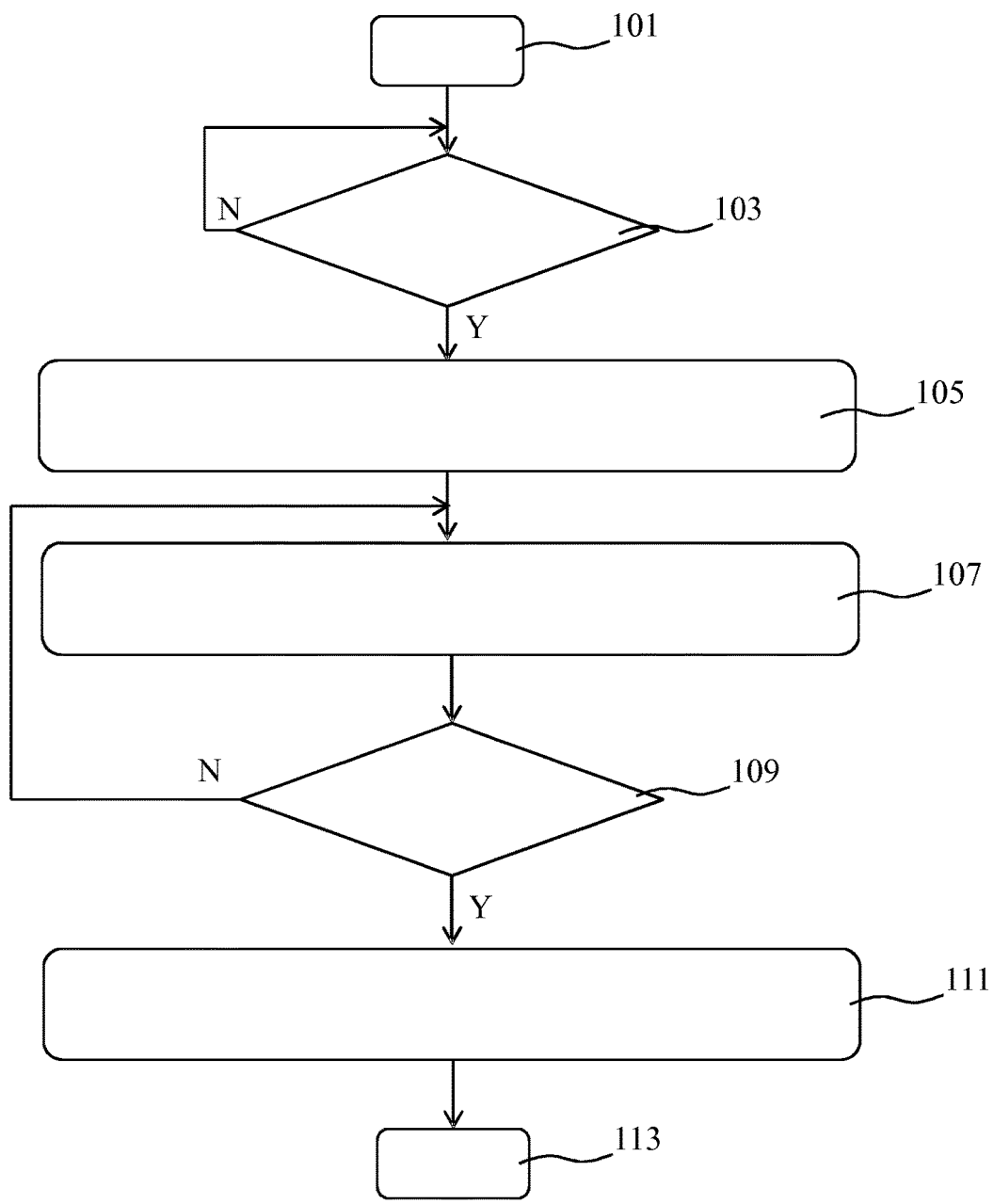
FIG. 9 is a flowchart of a sleep monitoring method according to an embodiment.

FIG. 9 is a flow chart of an example embodiment of a sleep monitoring method 100 of the present invention. The sleep monitoring method 100 starts in 101, e.g. by switching on or otherwise enabling a sleep monitoring system 10, after which the method proceeds to 103 in which it is determined if a monitored subject is attempting to sleep. Such an indication of the monitored subject adapted to sleep may be obtained by the monitored subject switching off a light, switching off a TV or radio, putting away a book providing a user input indicative of the monitored subject trying to go to sleep as previously explained. The method 100 stays in 103 until such an indication is obtained after which the method 100 proceeds to 105 in which $CO_2$ sensor data is collected in the confined space in which the monitored subject is attempting to sleep, preferably using a $CO_2$ sensor in close proximity to the monitored subject in order to improve the accuracy of the $CO_2$ sensor data.

The method 100 keeps collecting the received $CO_2$ sensor data over a period of time in 107 until an indication is received in 109 that the monitored subject's sleep has ended, i.e. that the subject is getting up. Such an indication may for instance be obtained by an alarm going off, a light being switched on, a sudden increase in the rate at which the $CO_2$ levels in the confined space increase, the monitored subject providing an indication on the user interface of a sleep monitoring system 10 that the subject has woken up, and so on. The method 100 subsequently proceeds to 111 in which the sleep efficiency of the monitored subject is derived from the collected indications and the collected $CO_2$ sensor data as explained in more detail above. Specifically, the above described sleep efficiency SE may be determined from the previously described $\Delta T_{total}$ and $\Delta T_{sleep}$, and the sleep onset latency SOL may be determined as described in more detail above. The method 100 may further generate a sensory output indicative of the sleep efficiency and/or sleep onset latency, for example by generating a visible message on a display device of an embodiment of the sleep monitoring system 10 described in more detail above, before the method 100 terminates in 113.

Figure 10:
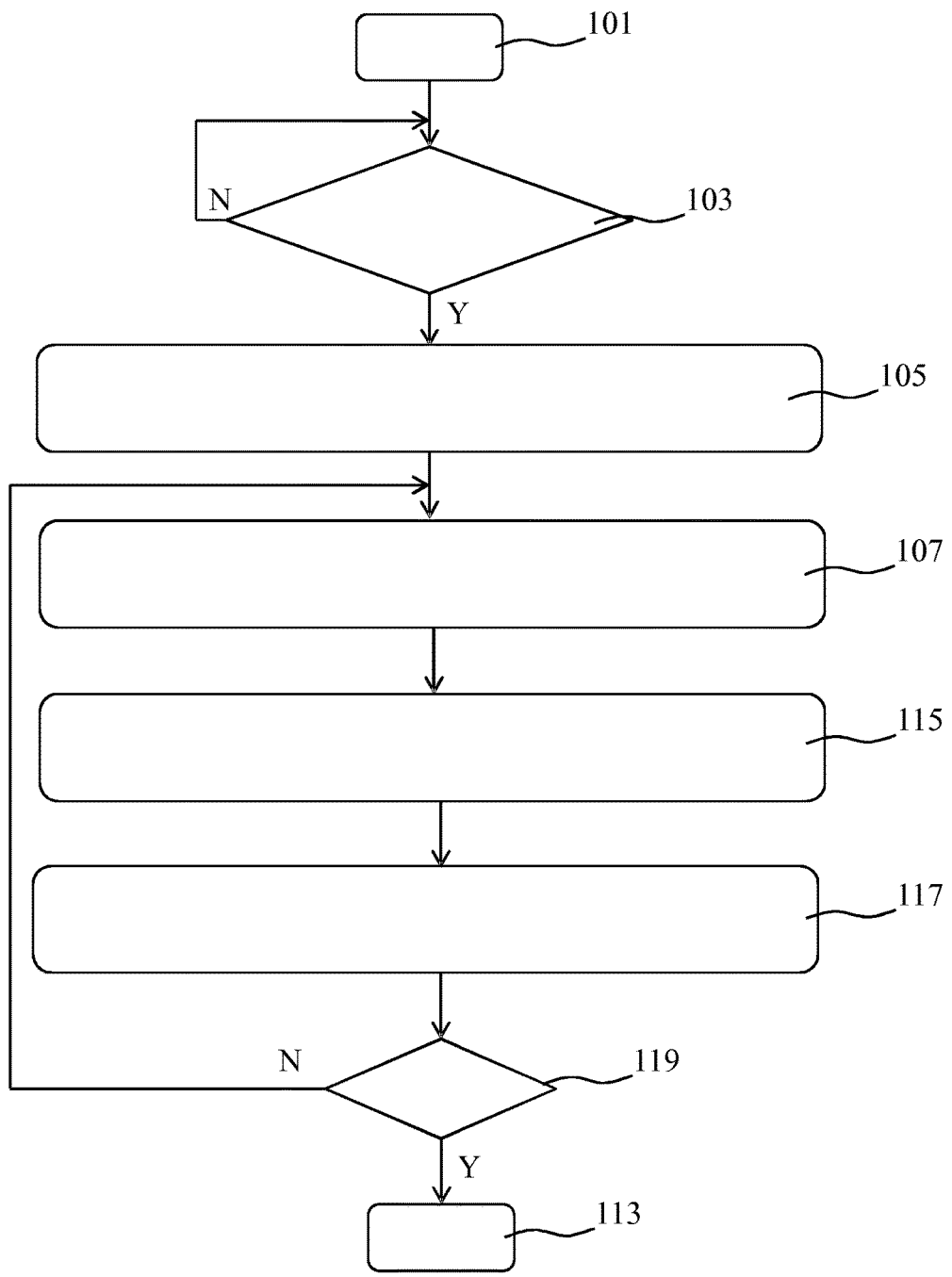
FIG. 10 is a flowchart of a sleep monitoring method according to an embodiment.

FIG. 10 is a flow chart of another example embodiment of a sleep monitoring method 100 of the present invention. In FIG. 10, steps 101, 103, 105 and 107 are identical to the steps of FIG. 9 and are therefore not described again for the sake of brevity. In the present embodiment, the $CO_2$ sensor data collected in 107 is utilized in 115 to determine a particular sleep phase of the monitored subject, e.g. whether the monitored subject is awake, in a state of light sleep or in a state of deep sleep, which may be derived by comparing the rate of increase of $CO_2$ levels in the confined space against a defined thresholds, e.g. Threshold 1 and Threshold 2, as explained in more detail above.

The identified sleep phase of the monitored subject may be used in 117 to trigger the generation of a sensory stimulus for the monitored subject that is specific to the identified sleep phase in order to enhance or improve the efficiency of that sleep phase, for example by generating a calming sound or pleasurable scent, by creating, dimming or disabling a light effect, by altering an air condition of the air in the confined space in which the monitored subject sleeping, and so on, as explained in more detail above. It is subsequently checked in 119 if the method may be terminated, e.g. because the monitored subject is waking up. If this is not the case, the method 100 may revert back to 107. Otherwise, the method may terminate in 113.

In an embodiment, a computer program product such as an app may be provided that can be installed on a computing device such as a mobile phone, tablet device, wearable smart device such as a smart watch, a personal computer, a laptop computer and so on, that allows a user to program embodiments of the sleep monitoring system 10. For example, such an app may facilitate the user to specify a particular (personalized) sleep atmosphere to be generated during the sleep of that user, which personalized sleep atmosphere may be communicated by the app to the sleep monitoring system 10 such that the sleep monitoring system 10 can generate the specified sensory stimuli at the appropriate point in time, i.e. during the various sleep phases of that user as specified with the app.

Aspects of the present invention may be embodied as sleep monitoring system 10 and a method 100 for monitoring the sleep of a subject. Aspects of the present invention may take the form of a computer program product embodied in one or more computer-readable medium(s) having computer readable program code embodied thereon. The code typically embodies computer-readable program instructions for, when executed on a processor 31 of such a sleep monitoring system 10, implementing the sleep monitoring method 100.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. Such a system, apparatus or device may be accessible over any suitable network connection;

for instance, the system, apparatus or device may be accessible over a network for retrieval of the computer readable program code over the network. Such a network may for instance be the Internet, a mobile communications network or the like. More specific examples (a non-exhaustive list) of the computer readable storage medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of the present application, a computer readable storage medium may be any tangible medium that can contain, or store a program for use by or in connection with an instruction execution system, apparatus, or device. A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out the methods of the present invention by execution on the processor 31 may be written in any combination of one or more programming languages, including an object oriented programming language such as Java, Smalltalk, C++ or the like and conventional procedural programming languages, such as the "C" programming language or similar programming languages. The program code may execute entirely on the processor 31 as a stand-alone software package, e.g. an app, or may be executed partly on the processor 31 and partly on a remote server. In the latter scenario, the remote server may be connected to the sleep monitoring system 10 through any type of network, including a local area network (LAN) or a wide area network (WAN), or the connection may be made to an external computer, e.g. through the Internet using an Internet Service Provider.

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions to be executed in whole or in part on the processor 31 of the sleep monitoring system 10, such that the instructions create means for implementing the functions/acts specified in the flowchart and/or block diagram block or blocks. These computer program instructions may also be stored in a computer-readable medium that can direct the sleep monitoring system 10 to function in a particular manner.

The computer program instructions may be loaded onto the processor 31 to cause a series of operational steps to be performed on the processor 31, to produce a computer-implemented process such that the instructions which execute on the processor 31 provide processes for implementing the functions/acts specified in the flowchart and/or block diagram block or blocks. The computer program product may form part of the sleep monitoring system 10, e.g. may be installed on the sleep monitoring system 10.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A sleep monitoring system for monitoring the sleep of a subject, comprising:
a $CO_2$ sensor for producing sensor data; and
a processor communicatively coupled to the $CO_2$ sensor, wherein the processor is adapted to:
monitor a $CO_2$ concentration from sensor data produced by the $CO_2$ sensor and derive sleep pattern information from the monitored $CO_2$ concentration, wherein the sleep pattern information comprises at least an indication that the subject is awake and an indication that the subject is asleep;

wherein, the processor is further adapted to:

provide an indication that the subject is awake when a rate of increase in the monitored $CO_2$ concentration is greater than a first threshold, and provide an indication that the subject is asleep when the rate of increase in the monitored $CO_2$ concentration is below the first threshold, further comprising:

an output device communicatively coupled to the processor for creating a sensory stimulus for the subject in response to a control signal generated by the processor, wherein the processor generates the control signal in response to the sleep pattern information that comprises at least the indication that the subject is awake and the indication that the subject is asleep.

2. The sleep monitoring system of claim 1, further comprising a further sensor for producing an indication that the subject is attempting to sleep, wherein the processor is adapted to derive sleep pattern information from sensor data produced by the $CO_2$ sensor and the further sensor.

3. The sleep monitoring system of claim 2, wherein the sleep pattern information further comprises an indication of sleep efficiency, wherein the processor is adapted to calculate the indication of the sleep efficiency from:

a first time period initiated by the indication that the subject is attempting to sleep and terminated by an indication that the subject is getting up; and a second time period initiated by an indication that the subject is asleep and terminated by an indication that the subject is awake that follows the indication that the subject is asleep.

4. The sleep monitoring system of claim 2, wherein the further sensor is a light sensor, a sound sensor or a user interface sensor.

5. The sleep monitoring system of claim 1, wherein the processor is further adapted to identify a sleep phase from said sensor data for the subject from the monitored $CO_2$ concentration, wherein the processor is adapted to:

identify that the subject is awake when a rate of increase in the monitored $CO_2$ concentration is greater than the first threshold;

identify a light sleep phase when a rate of increase in the monitored $CO_2$ concentration is between the first threshold and a second threshold; and identify a deep sleep phase when a rate of increase in the monitored $CO_2$ concentration is below the second threshold.

6. The sleep monitoring system of claim 5, wherein the processor is further adapted to generate a control signal for the output device in response to an identified sleep phase, wherein the output device comprises at least one of a scent releasing device, an audio output device and a light output device.

7. The sleep monitoring system of claim 6, wherein the processor is further adapted to generate a control signal for the output device by a defined amount of time prior to a wake-up time of the subject.

8. The sleep monitoring system of claim 7, comprising at least one of:

a plurality of different output devices for creating respective sensory stimuli, wherein processor is further adapted to generate a control signal for one or more selected output devices as a function of the identified sleep phase; and a fan, wherein the processor is further adapted to generate a further control signal for said fan in response to an identified sleep phase.

9. The sleep monitoring system of claim 8, wherein the sleep monitoring system is at least partially comprised by one selected from the group consisting of an air conditioning apparatus, an air purification apparatus, a respirator apparatus, and a humidification apparatus.

10. The sleep monitoring system of claim 1, wherein the $CO_2$ sensor is embodied in a first device and wherein the processor is embodied in a second device, wherein each of the first device and the second device further comprise a wireless communication module for establishing a wireless communication link between the first device and the second device.

11. The sleep monitoring system of claim 10, wherein the second device is a wearable device or a mobile communication device.

12. The sleep monitoring system of claim 1, wherein the processor is adapted to determine the first threshold by in-situ calibration of the sleep monitoring system.

13. The sleep monitoring system of claim 1, wherein the output device comprises at least one of a scent releasing device, an audio output device and a light output device.

14. A method of monitoring the sleep of a subject, the method comprising:

receiving, via a $CO_2$ sensor, a measured $CO_2$ concentration;

deriving, via a processor communicatively coupled to the $CO_2$ sensor, sleep pattern information from the measured $CO_2$ concentration, wherein the sleep pattern information comprises providing at least an indication that the subject is awake and an indication that the subject is asleep;

wherein:

deriving said sleep pattern information comprises:

providing, via the processor, an indication that the subject is awake when a rate of increase in the monitored $CO_2$ concentration is greater than a first threshold; and providing, via the processor, an indication that the subject is asleep when the rate of increase in the monitored $CO_2$ concentration is below the first threshold, the method further comprising:

generating, via the processor, a control signal in response to the sleep pattern information that comprises at least the indication that the subject is awake and the indication that the subject is asleep; and creating, via an output device communicatively coupled to the processor, a sensory stimulus for the subject in response to the control signal generated by the processor.

15. The method of claim 14, wherein deriving sleep pattern information comprises determining a sleep efficiency or determining a sleep phase of said subject.

16. The method of claim 15, wherein determining a sleep efficiency comprises:

calculating an indication of the sleep efficiency from:

a first time period initiated by an indication that the subject is attempting to sleep and terminated by an indication that the subject is getting up; and a second time period initiated by an indication that the subject is asleep and terminated by an indication that the subject is awake that follows the indication that the subject is asleep.

17. A non-transitory computer readable storage medium embodied with a computer program that comprises computer readable program instructions executable by a processor for enabling the processor to implement the method of monitoring the sleep of a subject as claimed in claim 14.

\* \* \* \* \*